(12) United States Patent
Kakimi et al.

(10) Patent No.: US 6,432,089 B1
(45) Date of Patent: Aug. 13, 2002

(54) MEDICAL SYRINGE

(75) Inventors: Mitsuru Kakimi, Hyogo (JP); Mark Hitchins, Sewickley, PA (US)

(73) Assignee: Medrad, Inc., Indianola, PA (US)

( * ) Notice: Subject to any disclaimer, the term of this patent is extended or adjusted under 35 U.S.C. 154(b) by 149 days.

(21) Appl. No.: 09/598,628

(22) Filed: Jun. 21, 2000

(51) Int. Cl.[7] .............................................. A61M 5/315
(52) U.S. Cl. ...................................................... 604/218
(58) Field of Search ................................ 604/222, 230, 604/218, 187, 193, 215, 219–221, 228, 229; 222/135, 386

(56) References Cited

U.S. PATENT DOCUMENTS

| | | | |
|---|---|---|---|
| 4,006,736 A | | 2/1977 | Kranys et al. |
| 4,677,980 A | | 7/1987 | Reilly et al. |
| 4,911,695 A | * | 3/1990 | Lindner ................. 600/432 |
| 5,007,904 A | * | 4/1991 | Densmore et al. ........ 600/432 |
| 5,300,031 A | | 4/1994 | Neer et al. |
| 5,314,415 A | * | 5/1994 | Liebert et al. ............. 604/218 |
| 5,353,691 A | | 10/1994 | Haber et al. |
| 5,383,858 A | | 1/1995 | Reilly et al. |
| 5,785,682 A | | 7/1998 | Grabenkort |
| 5,902,276 A | | 5/1999 | Namey, Jr. |
| 5,947,929 A | | 9/1999 | Trull |

FOREIGN PATENT DOCUMENTS

| | | |
|---|---|---|
| EP | 1 002 551 | 5/2000 |
| WO | WO 98/20920 | 5/1998 |

* cited by examiner

*Primary Examiner*—Brian L. Casler
*Assistant Examiner*—Cris L. Rodriguez
(74) *Attorney, Agent, or Firm*—Gregory L. Bradley (57) ABSTRACT

A medical syringe 2 includes a cylindrical syringe body 3 and a plunger 4 fitted in the syringe body 3 for injecting a liquid agent filled in the syringe body 3 from the syringe body 3 into the vascular system of the human body by advancing the plunger 4 relative to the syringe body 3. The plunger 4 comprising a plunger body 5 and an elastic cover 9 fitted over the plunger body 5 from the front. The plunger body 5 is provided with a backplate 62 at a rear end thereof, the backplate 62 having an annular groove 68 forwardly opened and formed in a front surface outer peripheral portion thereof. The portion of the elastic cover 9 to be rearwardly stretched by the advance of the plunger 4 is allowed to ingress into the annular groove 68 for escape.

5 Claims, 10 Drawing Sheets

MEDICAL SYRINGE

FIELD OF THE INVENTION

The present invention relates to syringes fillable with a liquid agent for use as attached to injectors for medical procedures, such as angiography, computerized tomography, NMR/MRI, etc., to be performed with a contrast medium, chemical agent or like liquid agent injected into the vascular system of the human body or an animal.

BACKGROUND OF THE INVENTION

As disclosed in U.S. Pat. No. 4,006,736, syringes for use in examining patients in medical procedures are used by attaching the main body of the syringe to an injector and fixing a plunger fitted in the syringe body in intimate contact therewith to a piston of the injector. The piston advances at a speed controlled by a control circuit of the injector, pushing the plunger to inject a liquid agent filled in the syringe into the vascular system of the patient.

Further, U.S. Pat. No. 4,677,980 discloses a syringe including a plunger which is connectable to a piston or disconnectable therefrom by rotating the entire syringe through about 90 deg relative to the piston, with the plunger held in contact with the forward end of the piston.

Figure 10:
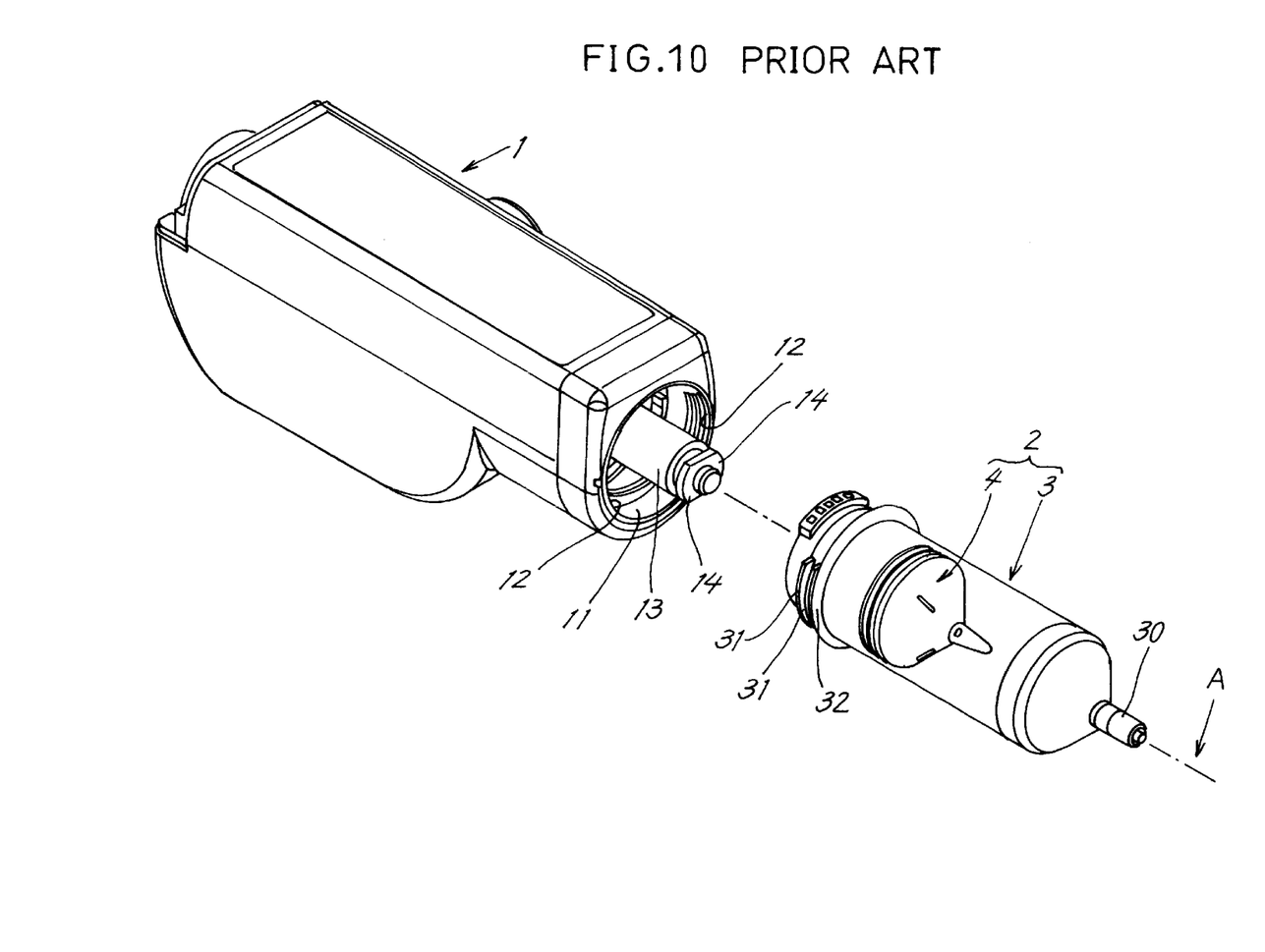
FIG. 10 is a perspective view showing an injector and a syringe of the prior art.
Figure 11:
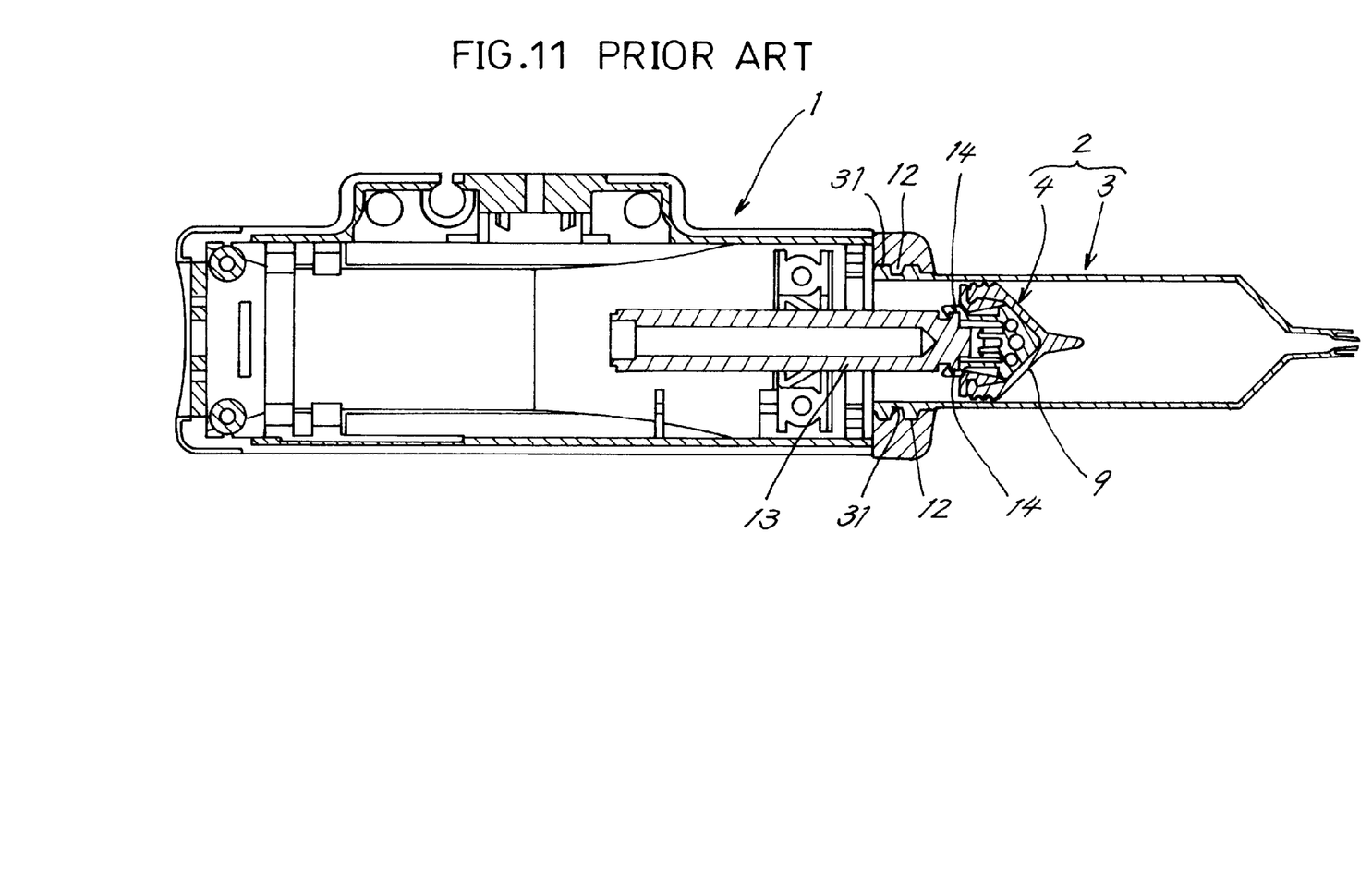
FIG. 11 is a sectional view showing the syringe as connected to the injector according to the prior art.

Further International Publication No. WO 98/20920 (corresponding to Japanese Patent Application No. 522638/1998) discloses a syringe 2 shown in FIGS. 10 and 11.

The syringe 2 comprises a cylindrical syringe body 3 and a plunger 4 fitted in the syringe body. The syringe 2 is connected to an injector 1 by removably fixing a base end of the syringe body 3 in a syringe socket 11 of the injector 1 and releasably engaging the plunger 4 of the syringe 2 with a piston 13 which is movable out of or into the socket 11 centrally thereof. The piston 13 is projected outward at a controlled speed by a drive device (not shown) incorporated in the injector 1, thereby advancing the plunger 4 toward the forward end of the syringe body 3 to inject a liquid agent filled in the syringe body 3 into the vascular system of the human body or an animal through a tube (not shown) from a nozzle 30 at the front end of the syringe body 3.

In the following description, the term "front" or "forward" refers to one side of the syringe 2 where the syringe body 3 is connected to the patient and the liquid agent is forced out by the plunger 4, and the term "rear" or "rearward" refers to the other side opposite to the above side where the syringe is connected to the injector.

The inner periphery of the socket 11 of the injector 1 is provided with syringe holding flanges 12, 12. Projecting from the syringe body 3 radially thereof are ridges 31 engageable with the flanges 12, 12 and a flange 32 adapted for bearing contact with the end face of the socket 11.

The piston 13 is provided at its front end with plunger holding pieces 14, 14 orthogonal to the axis of the piston 13.

Figure 13:
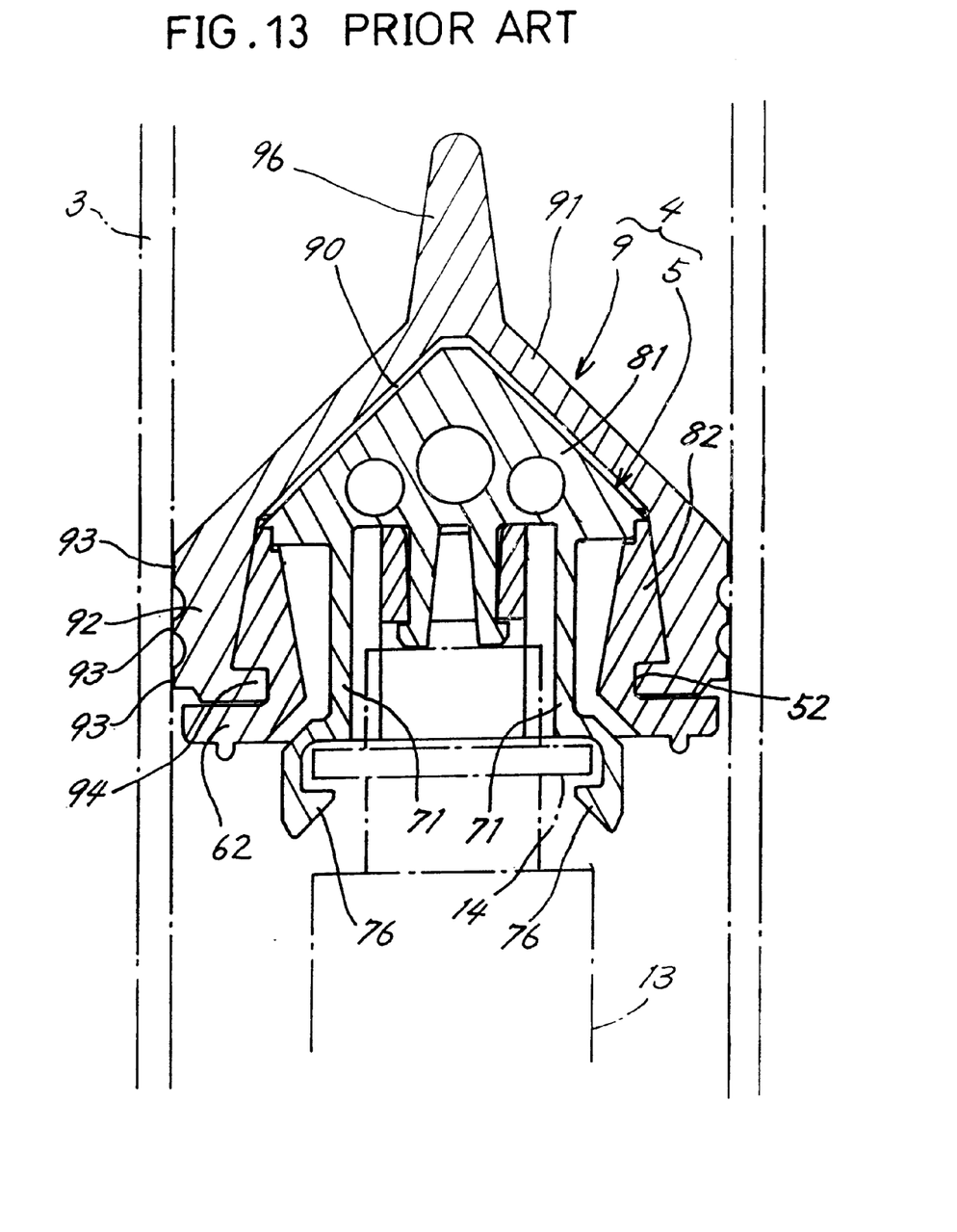
FIG. 13 is a sectional view of a conventional plunger.

With reference to FIG. 13, the plunger 4 disclosed in the foregoing publication WO No. 98/20920 comprises a plunger body 5 and an elastic cover 9 fitted over the body 5.

The plunger body 5 comprises two members which are fitted together, i.e., a conical portion 81 at the front end, and a hollow truncated cone 82 fitted to the conical portion 81, extending rearward and having a gently tapered conical surface.

A circular backplate 62 extends from the rear end of the truncated cone 82 radially thereof, with a recessed portion 52 formed between the backplate 62 and the cone 82 over the entire circumference thereof.

Projecting rearward from the rear end of the conical portion 81 are a pair of connecting legs 71, 71 each having an inward claw 76.

The elastic cover 9 is fitted over the plunger body 5 to extend over the conical portion 81 thereof to the recessed portion 52, and comprises a hollow conical portion 91, a cylindrical portion 92 extending from the conical portion 91, an inward flange 94 projecting from the rear end of the cylindrical portion 92 and a projection 96 extending forward from the front end of the conical portion 91. A plurality of ribs 93, 93 are formed on the outer peripheral surface of the cylindrical portion 92 over the entire circumference thereof.

The projection 96 is positioned in the tubular nozzle 30 at the front end of the syringe body 3 on completion of advance of the plunger 4, minimizing the quantity of the liquid agent remaining within the syringe body 3 and to be wasted.

The hollow conical portion 91 of the elastic cover 9 covers the conical portion 81 of the plunger body 5 with a small space 90 left therebetween. The cylindrical portion 92 covers the truncated cone 82 in intimate contact therewith, with the inward flange 94 fitting in the recessed portion 52 around the cone 82.

The syringe body 3 is fitted at its base end into the socket 11 of the injector 1 and then rotated through about 90 deg to position the ridge 31 of the syringe body 3 inside the syringe holding flange 12 formed on the inner surface of the socket 11, whereby the syringe body 3 is prevented from slipping out of the socket 11.

The piston 13 of the injector 1 as retracted is positioned away from the plunger 4 of the syringe 2. When the piston 13 is projected outward gradually, however, the holding pieces 14, 14 at the front end of the piston force the pair of legs 71, 71, projecting from the rear side of the plunger 4, away from each other and are brought into engagement with the claws 76, 76 at the front side thereof (see FIG. 13). Since the front end face of the piston 13 comes into pushing contact with the plunger body 3, the plunger 4 advances, whereby the liquid agent in the syringe 2 is injected into the vascular system of the human body or animal as described above.

To remove the syringe 2 from the injector 1 after it is used for injecting the liquid agent, the syringe body 3 is rotated through about 90 deg in a direction opposite to the direction in which the body is rotated for connection. This releases the ridge 31 of the syringe body 3 from engagement with the syringe holding flange 12 of the injector socket 11 and the claws 76, 76 of the plunger 4 from engagement with the holding pieces 14, 14 of the piston 13. The syringe 2 is removed from the socket 11.

Figure 12:
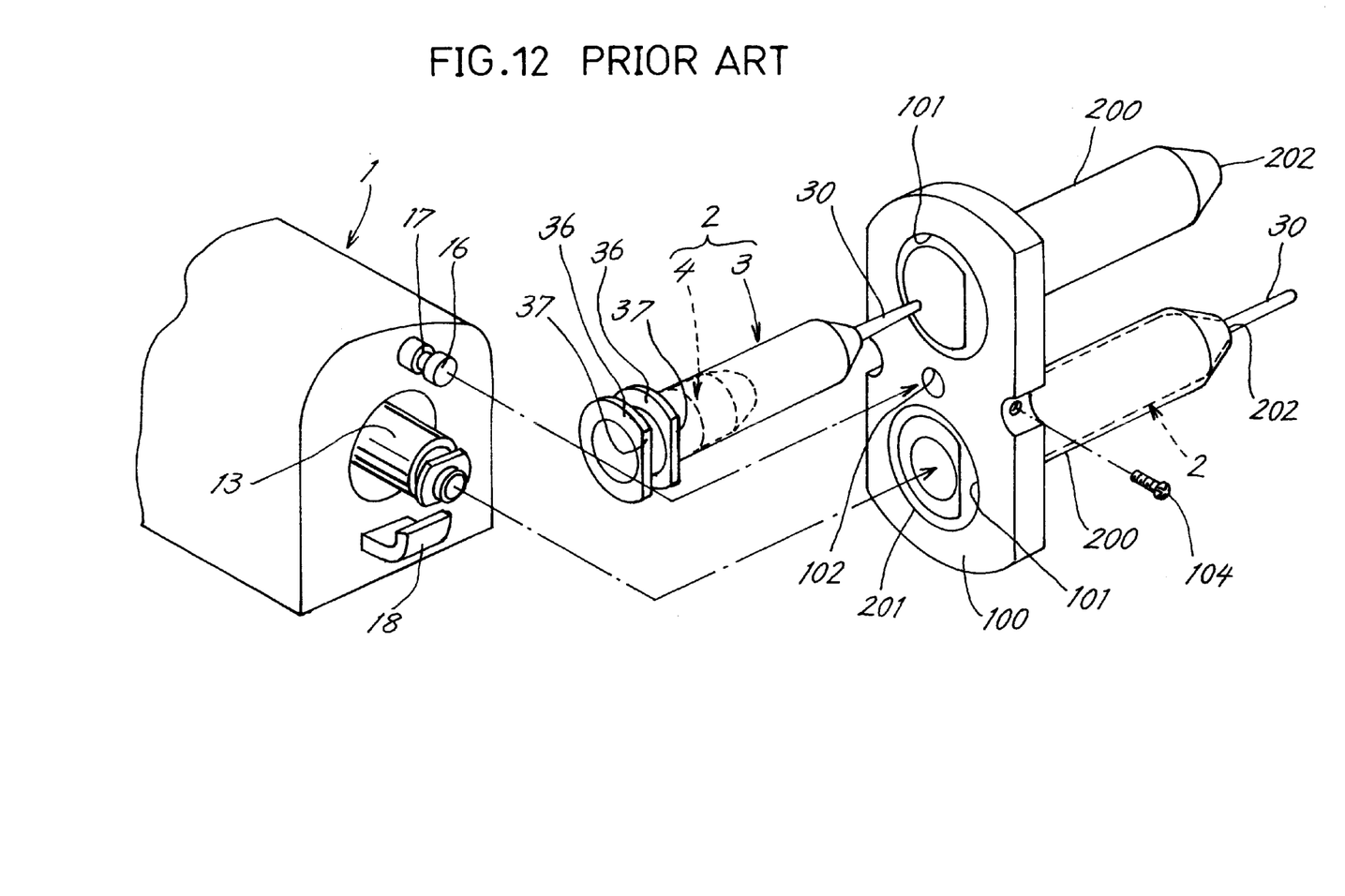
FIG. 12 is a perspective view showing a conventional syringe for use as sheathed in a reinforcing case and means for mounting the combination.

The syringe 2 shown in FIG. 11 and described above needs to be so designed as to withstand the pressure of injecting the liquid agent. As shown in FIG. 12, such a syringe 2 is also used as sheathed in a reinforcing case 200 on a turret 100 for connection to an injector 1.

Like the foregoing one, this type of syringe 2 comprises a syringe body 3 and a plunger 4, whereas the syringe body 3 need not withstand the internal pressure involved in injecting the liquid agent but has characteristics to slightly expand under the internal pressure.

The syringe body 3 is provided at its rear end with parallel flanges 36, 36 each having a cut portion 37 for preventing rotation. The syringe 2 is removably fitted into the case or pressure jacket 200 supported by the turret 100 and is set in position.

The turret 100 has stepped through bores 101, 101 at opposite sides of a hole 102 which provides the center of rotation of the turret 100.

Tubular transparent reinforcing cases or pressure jackets 200, 200 are inserted from behind the turret 100 through the respective bores 101, 101 in the turret 100.

The reinforcing case 200 has a rear end provided with a flange 201 serving as a retainer and a front end tapered in the form of a cone and formed with a hole 202 for a nozzle 30 of the syringe body 3 to extend therethrough.

The injector 1 is provided with a turret rotating support pin 16 above a piston 13 and a turret receiving portion 18 below the piston 13.

The syringe 2 is inserted into one of the reinforcing cases 200 on the turret 100, the support pin 16 is fitted into the hole 102 in the turret 100, the forward end of a screw 104 driven into the turret 100 orthogonally to the hole 102 is fitted into a groove 17 in the support pin 16, and one end of the turret 100 is engaged with the receiving portion 18 projecting from the injector 1 to prevent the turret 100 from slipping off.

When the piston 13 is connected to the plunger 4 of the syringe 2 as inserted in the case 200, with the axis of the case 200 on the turret 100 aligned with the axis of the piston 13, another syringe 2 can be inserted into or removed from the other case 200.

The syringe body 3 is expanded into intimate contact with the inner surface of the reinforcing case 200 by the internal pressure acting on the syringe body 3 when the liquid agent in the syringe 2 is injected by the advancement of the piston 13. The syringe body 3 withstands the internal pressure of injection by virtue of the strength of the case or pressure jacket 200.

In the case of the syringe 2 shown in FIGS. 11 and 12 and described above, the cylindrical portion 92 of the elastic cover 9 fitting around the truncated cone 82 of the plunger body 5 is brought into intensely frictional contact with the inner surface of the syringe body 3 when the plunger 4 advances as shown in FIG. 13, with the result that the conical portion 91 of the cover stretches toward a rearwardly tapered region between the inner surface of the syringe body 3 and the truncated portion 82 of the plunger body 5, producing an effect achieved as by forcing in a wedge (hereinafter referred to as a "wedging effect"). The elastic material in this region is compressed to a higher degree, making it possible to inject the liquid agent within the syringe body 3 into the vascular system of the human body or animal at a higher pressure than conventionally. Accordingly, the liquid agent can be injected into arterial vessels at a pressure higher than arterial blood pressure.

However, higher pressures impose limitations on the operation of the syringe 2 although it is adapted for high-pressure injection.

When the internal pressure of the syringe 2 is increased by the advance of the plunger 4, an enhanced wedging effect presses the elastic cover 9 against the inner surface of the syringe body 3 with a greater force, whereby the cylindrical portion 92 of the cover 9 is compressed under higher pressure and becomes seriously impaired in slipperiness.

The elastic cover 9 is stretched further rearward by the advance of the piston 13, but blocked by the backplate 62 and forced into a minute clearance between the periphery of the backplate 62 and the inner surface of the syringe body 3. This entails the problem that the portion of the cover 9 forced in has its surface scraped off in a very small amount by pressing contact with the syringe body 3, leaving scraped-off minute fragments on the syringe body inner surface during continued injection. Furthermore, the elastic cover 9 thus forced in offers excessive resistance to the advancement of the plunger 4.

SUMMARY OF THE INVENTION

In view of the foregoing problems, the present invention provides a syringe which is usable for high-pressure injection without permitting an elastic plunger cover to release scraped-off minute fragments thereof into the syringe while allowing the plunger to advance therein.

The present invention provides a medical syringe 2 comprising a cylindrical syringe body 3 and a plunger 4 fitted in the syringe body 3 for injecting a liquid agent filled in the syringe body 3 from the syringe body 3 into the vascular system of a human body or animal by advancing the plunger 4 relative to the syringe body 3, the plunger 4 comprising a plunger body 5 and an elastic cover 9 fitted over the plunger body 5 from the front, the plunger body 5 being provided with a backplate 62 at a rear end thereof, the backplate 62 having an annular groove 68 forwardly opened and formed in a front surface thereof in the vicinity of an outer periphery thereof.

When the plunger 4 is pushed under high pressure against arterial blood pressure, the elastic cover 9 over the plunger body 5 stretches rearward in sliding contact therewith and is forced in between the plunger body 5 and the inner surface of the syringe body 3 and thereby compressed to a higher degree to produce an enhanced sealing effect. Although the rear end of the elastic cover 9 is stretched rearward by the advance of the plunger 4, the stretched portion is allowed to escape into the annular groove 68 forwardly opened and formed in the front surface outer peripheral portion of the backplate 62.

An outer annular wall 68c defining the annular groove 68 serves to guide the outer periphery of the rearwardly stretched portion of the elastic cover 9 toward the annular groove 68.

This eliminates the conventional likelihood that the rearwardly stretched cover portion will wedge into the very small clearance between the outer periphery of the backplate 62 and the inner surface of the syringe body 3 during the advance of the plunger 4, producing minute scraped-off fragments and causing troubles such as the failure of the plunger 4 to advance.

The base end of the elastic cover 9 escaping into the annular groove 68 fills up the groove 68, pressing the inner surface of the syringe body 3 to achieve a further improved sealing effect.

The liquid agent within the syringe body 3 can be injected into the vascular system of the human body or animal with an exceedingly higher pressure than is the case with the syringe 2 disclosed in International Publication No. WO98/20920 described, by virtue of the function of the annular groove 68 of the plunger 4. A high pressure is available in the range of 87 kg/cm$^2$ to 98 kg/cm$^2$ without entailing problems such as the release of scraped-off fragments of the elastic cover 9 of the plunger 4 and the failure of the plunger 4 to advance.

When the rear end face of the elastic cover 9 is formed with an annular ridge 95 concentric with the cover, the ridge 95 can easily escape into the annular groove 68 when the rear end of the elastic cover 9 is stretched rearward by the advance of the plunger 4.

When the plunger body 5 has a recessed portion 52 formed in the periphery of a rear portion thereof and continuous with the opening of the annular groove 58 of the backplate 62, the elastic cover 9 can be prevented from slipping off the plunger body 5 by fitting an inward flange 94 formed on the inner surface of the elastic cover 9 into the recessed portion 52, before the plunger body 5 is fitted into the syringe body 3 in the assembling step.

When the annular groove 68 formed in the front surface of the backplate 62 is so shaped in cross section that opposite side faces defining the groove 68 are inclined or curved toward each other to give the groove a width decreasing toward its bottom, the backplate 62 can be given an increased strength without giving an increased thickness to the groove-defining walls of the backplate.

Further when the annular groove 68 is shaped in conformity with the shape of the annular ridge 95 at the rear end of the elastic cover 9 in cross section, the inclination of the groove-defining side faces 68a, 68b enables the annular ridge 95 to ingress into the groove 68 for escape with greater ease.

It is desired to mold the elastic cover 9 from a composition which has incorporated therein a material, such as paraffin wax or polyethylene, having solid lubricity, or a composition which has incorporated therein a superfine spherical lubricating component of polyethylene, nylon, Teflon or like synthetic resin. The elastic cover 9 is then slidable on the inner surface of the syringe body 3 with improved smoothness to reduce the resistance to the injection by the plunger.

DETAILED DESCRIPTION OF THE PREFERRED EMBODIMENT

The syringe 2 of the invention is characterized by the plunger 4 to be fitted in the body 3 of the syringe.

The means for connecting the syringe 2 to an injector 1 is not limited to the one shown in FIGS. 10 and 11 or to the one comprising the turret 100 shown in FIG. 12. Any connecting means is usable insofar as it is so constructed that the syringe body 3 can be supported directly or indirectly by the injector for a piston 13 to push the plunger 4.

Figure 1:
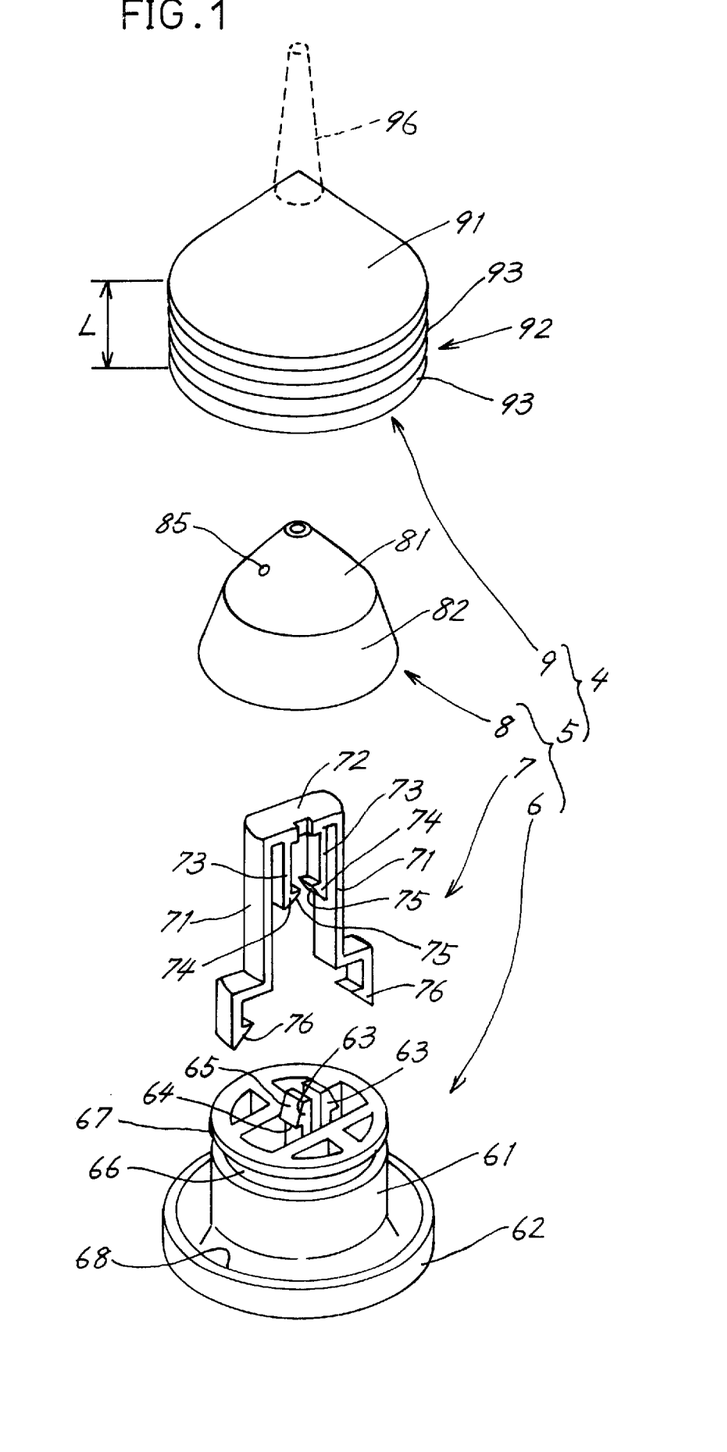
FIG. 1 is an exploded perspective view of a plunger.
Figure 2:
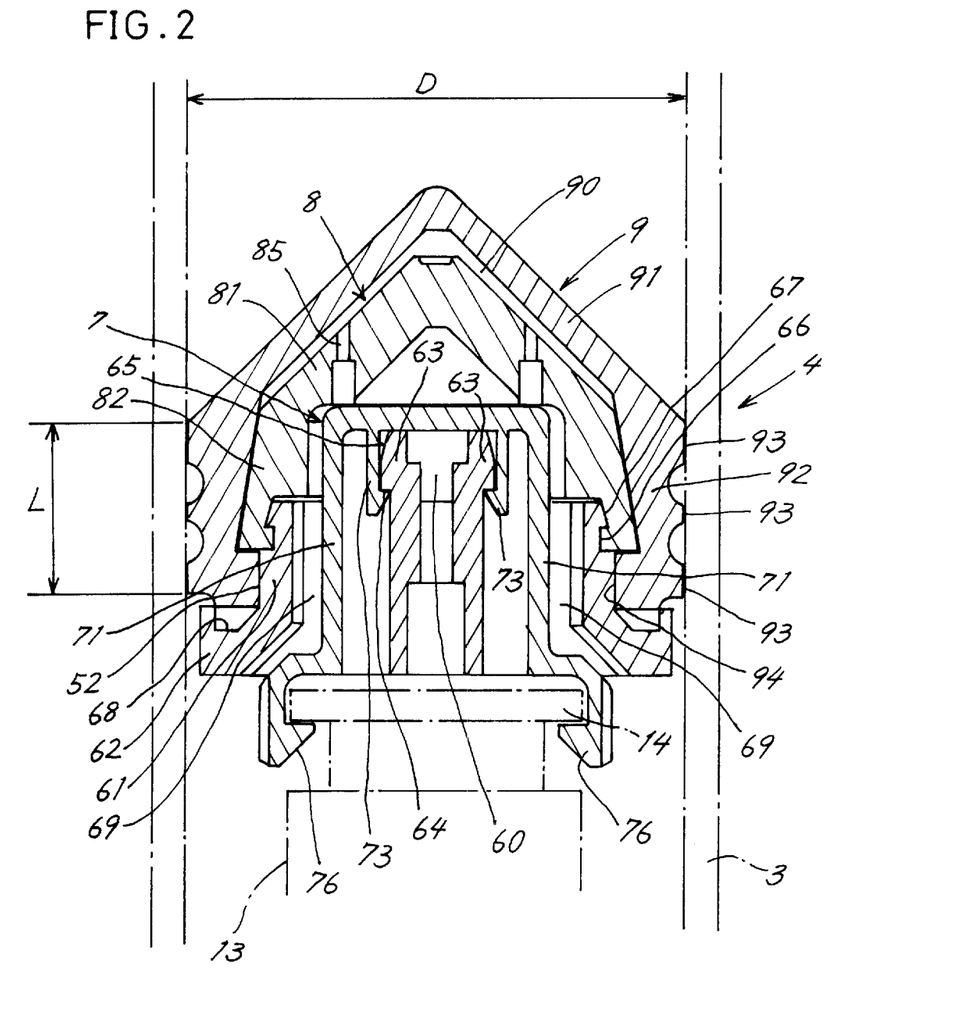
FIG. 2 is a sectional view of the plunger.

With reference to FIGS. 1 and 2, the plunger 4 comprises a plunger body 5 made from a synthetic resin, and an elastic cover 9 fitted over the plunger body.

The plunger body 5 has a conical portion 81 at its front end, a hollow truncated cone 82 integral with the conical portion 81, positioned at a rear portion thereof and formed with a surface tapered at a smaller angle than the conical portion 81, and a backplate 62 at its rear end.

The backplate 62 has a diameter greater than the maximum diameter of the truncated cone 82.

The plunger body 5 has a recessed portion 52 formed between the backplate 62 and the truncated cone 82 and extending over the entire circumference thereof.

The plunger body 5 may be composed integrally of the conical portion 81, truncated cone 82 and backplate 62, whereas according to the illustrated embodiment, the backplate 62 is formed as a separate part and fitted in the truncated cone 82 to ensure a convenient molding operation as will be described later.

The truncated cone 82 is internally provided with a pair of connecting legs 71, 71 extending rearward from the rear end face of the plunger body 5 and each having an inward claw 76 at its rear end.

An annular groove 68 concentric with the truncated cone 82 is formed in an outer peripheral portion of the front surface of the backplate 62 for receiving the portion of the elastic cover 92 which stretches rearward when the plunger 4 advances.

According to the embodiment, the diameter of inner periphery of the annular groove 68 is smaller than the maximum diameter of the truncated cone 82. Accordingly, if the plunger body 5 is be molded integrally and when the mold is to be opened along a plane containing the center axis of the body, the annular groove 68 corresponds to an undercut, with the result that the plunger body 5 is not moldable as a single part.

According to the embodiment, the plunger body 5 comprises three components, i.e., a first component 6, second component 7 and third component 8, each of which is formed from synthetic resin by injection molding and which are fitted to one anther as arranged axially thereof.

First, Second and Third Components

The first component 6 comprises a columnar portion 61 having a short axial length, and a backplate 62 formed at the base end of the columnar portion 61 concentrically therewith and having a diameter greater than the diameter of the portion 61 but slightly smaller than the inside diameter of the syringe body 3.

The first component 6 is generally shown in FIGS. 4 to 7. The columnar portion 61 has a pair of projections 63, 63 projecting from its front end and positioned at opposite sides of the axis of the portion 61 on a diametrical line thereof. Spaces 60, 69 extending through the columnar portion 61 axially thereof are formed respectively between the projections 63, 63 and between each projection 63 and the peripheral wall of the portion 61.

Each projection 63 has an engaging stepped portion 64 formed in its back, and a guide face 65 inwardly inclined and extending from the stepped portion 64 to its front end.

The columnar portion 61 has a circumferential groove 66 formed in the outer periphery of a front portion thereof, and a tapered surface 67 extending from the groove 66 to the front edge of the portion 61 with a gradually decreasing diameter.

Figure 3:
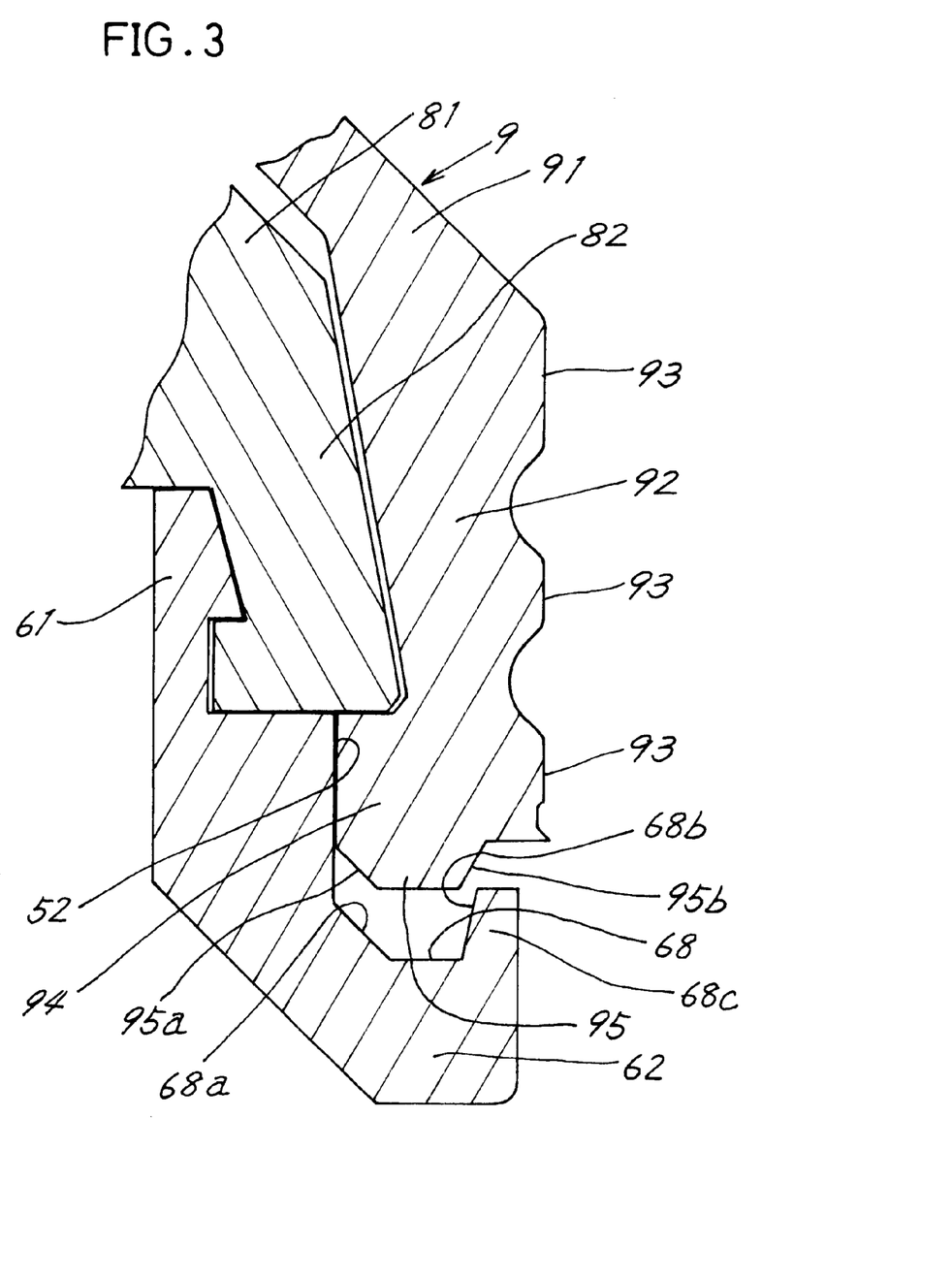
FIG. 3 is a sectional view of the position relationship between an annular groove of the plunger and the rear end of an elastic cover in a load-free state.
Figure 4:
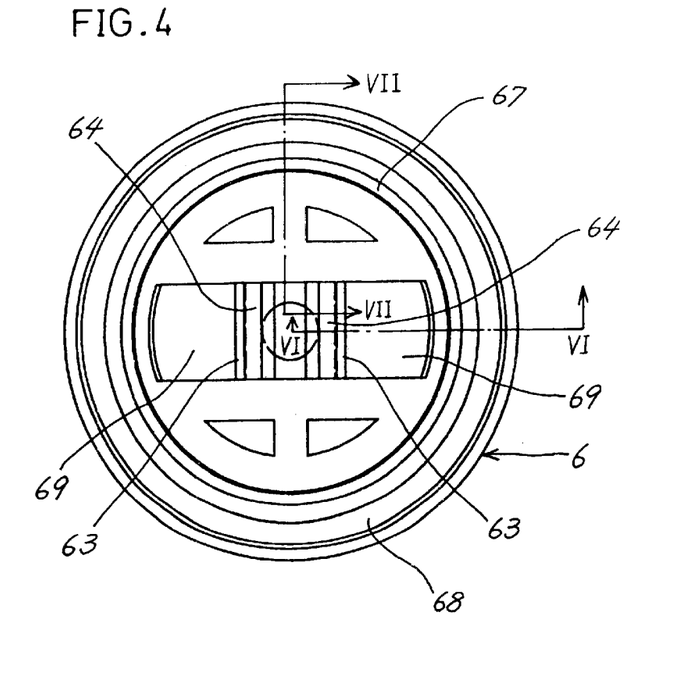
FIG. 4 is a plan view of a first component.
Figure 5:
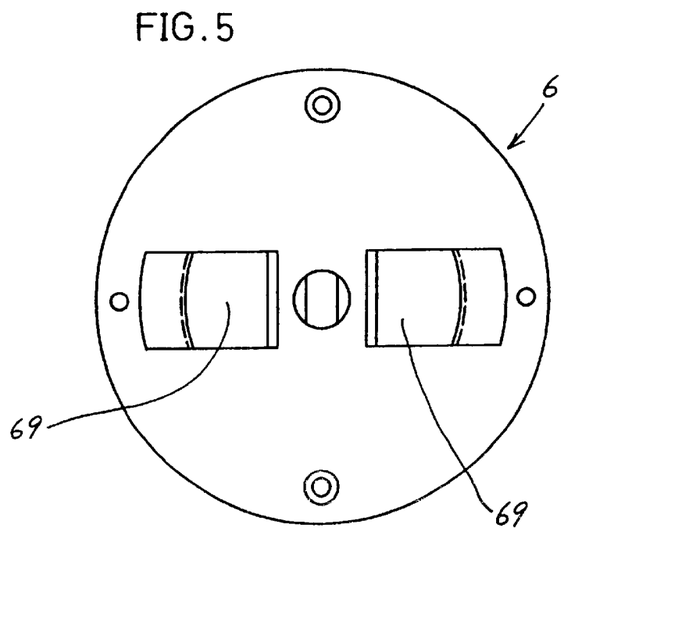
FIG. 5 is a bottom view of the first component.
Figure 6:
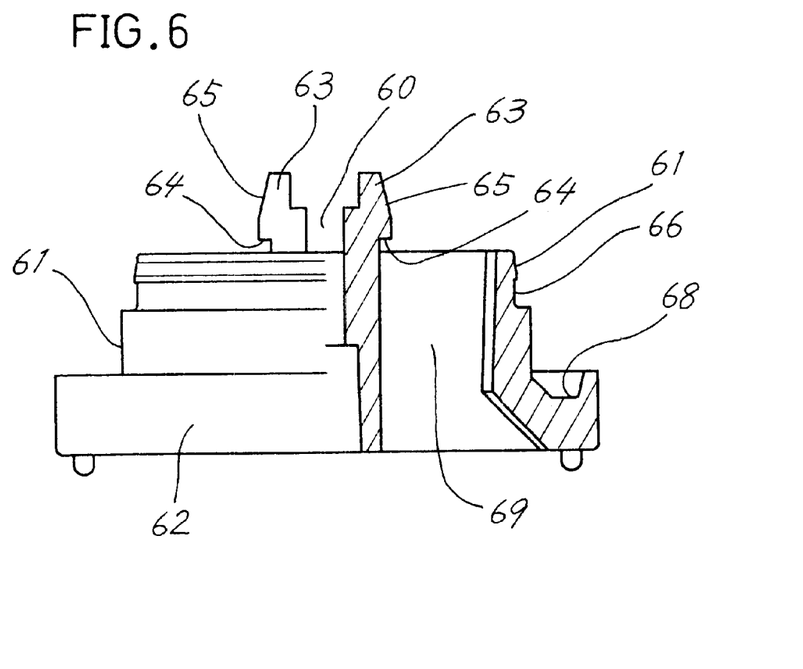
FIG. 6 is a front view showing the first component partly in section taken along the line VI—VI in FIG. 4.
Figure 7:
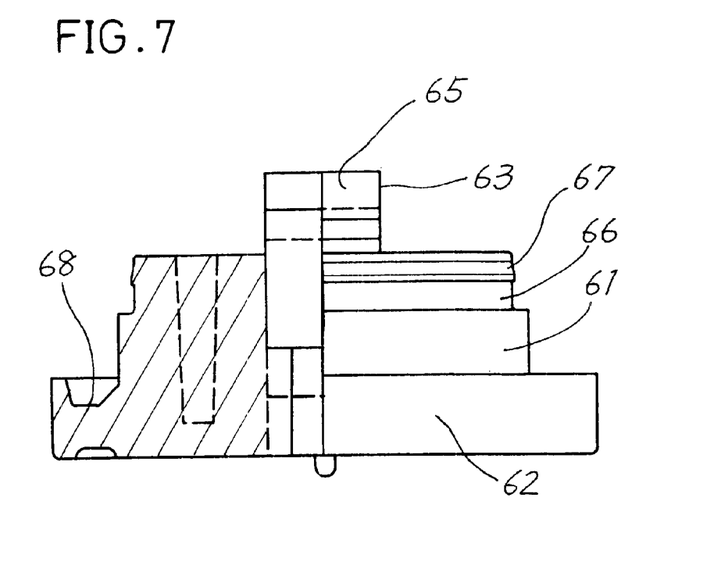
FIG. 7 is a side elevation showing the first component partly in section taken along the line VII—VII in FIG. 4.

With reference to FIG. 3, the aforementioned annular groove 68 formed in the front surface of the backplate 62 integral with the columnar portion 61 is so shaped in cross section that opposite side faces 68a, 68b defining the groove 68 are inclined toward each other to give the groove a width decreasing toward its bottom. The inner peripheral side face 68a defining the groove 68 is inclined more gently than the outer peripheral side face 68b.

The outer annular wall 68c thus inclined to define the annular groove 68 therefore has a wall thickness gradually decreasing toward the opening side of the groove 68.

The annular groove 68 has such a volume that the portion of the elastic cover 9 which is stretched rearward by the advance of the plunger 4 ingresses into and fills the groove 68 as will be described later.

With reference to FIGS. 1 and 2, the second component 7 has two legs 71, 71 which are arranged in parallel as spaced apart by a greater distance than the pair of projections 63, 63 of the first component 6. The front ends of the legs 71, 71 are interconnected by a bar 72. Projecting rearward from the bar 72 are a pair of connecting pieces 73, 73 in parallel to the legs 71.

Each connecting piece 73 has at its rear end a hook 74 engageable with the stepped portion 64 of the projection 63 of the first component 6. The hook 74 is formed with a slope 75 inclined along the slope of the guide face 65 of the projection 63.

The legs 71, 71 of the second component 7 are flexible to move away from each other. Each leg 71 is provided at the rear end thereof with a claw 76 engageable with a plunger holding piece 14 of piston 13 of the injector 1.

Figure 8:
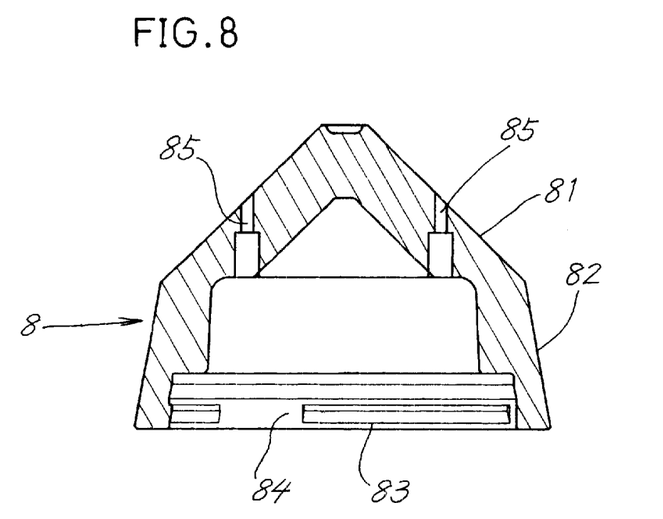
FIG. 8 is a sectional view of a third component.
Figure 9:
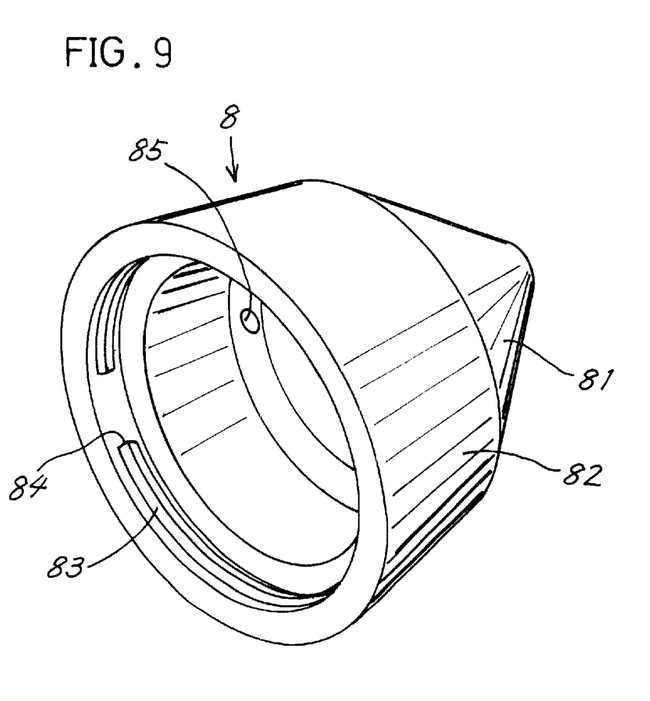
FIG. 9 is a perspective view of the third component as it is seen from the bottom side.

With reference to FIGS. 8 and 9, the third component 8 comprises a conical portion 81 and a truncated cone 82 integral therewith and is in the form of a hollow body having a flaring rear portion with an opening.

The conical portion 81 has an angle of about 45 deg with the axis thereof. The tapered surface of the truncated cone 82 has an angle in the range of 3 deg to 15 deg, preferably 4 deg to 10 deg, with the axis thereof.

The third component 8 has at its opening side a circumferential ridge 83 formed on the inner surface thereof and fittable in the circumferential groove 66 in the front end of columnar portion 61 of the first component 6.

The ridge 83 is not continuous in an annular form but is divided at a plurality of locations, i.e., at three portions according to the embodiment. At the divided portions, the third component 8 has a reduced wall thickness and is easily elastically deformable.

The third component 8 has air vents 85 extending through the conical portion 81.

Assembly of Plunger Body

To assemble the plunger body 5 as shown in FIG. 2, the legs 71, 71 of the second component 7 are inserted through the respective outer spaces 69, 69 of the first component 6 from the front while inwardly deflecting the legs to bring the connecting pieces 73, 73 of the second component 7 into bearing contact with the respective projections 63, 63. The second component 7 is further pushed in, whereby the connecting pieces 73, 73 are deflected outward, with the projections 63, 63 deflected inward, permitting the connecting pieces 73, 73 to be pushed in. Upon the hook 74 of each connecting piece 73 moving over the guide face 65 of the projection 63 to the stepped portion 64 thereof, the connecting piece 73 and the projection 63 restore themselves elastically, causing the hook 74 to engage in the stepped portion 64, whereby the first component 6 and the second component 7 are joined together.

The third component 8 is fitted to the first component 6 from the front.

The ridge 83 of the third component 8 comes into contact with the front-end tapered surface 67 of the columnar portion 61 of the first component 6. When further pressed on, the third component 8 elastically deforms at the divided portions of the ridge 83, permitting the ridge 83 to fit into the circumferential groove 66 of the first component 6. With the third component 8 joined to the first component 6, the plunger body 5 is completely assembled.

Elastic Cover

The elastic cover 9 is in the form of a hollow body having a conical portion 91, cylindrical portion 92 continuous with the portion 91, and inward flange 94 projecting from the rear end of the cylindrical portion 92 so as to cover the conical portion 81, truncated cone 82 and recessed portion 52 of the plunger body 5.

The cylindrical portion 92 has an inner peripheral surface which is inclined in conformity with the inclination of the truncated cone 82 of the third component 8. The cylindrical portion 92 has a wall thickness gradually decreasing toward the rear end thereof.

The cylindrical portion 92 is provided on its outer periphery with a plurality of, preferably at least three, ribs 93 for affording an effective liquid-tight seal to hold a liquid agent filled in the syringe body 4.

It is desired that the straight distance L from the front edge of the foremost rib to the rear edge of the rearmost rib be at least 30% of the inside diameter D of the syringe body 3 (L>0.3 D). This prevents the plunger 4 from inclining relative to the axis of the syringe body 3 during the movement of the plunger 4, enabling the plunger 4 to move smoothly.

As shown in FIG. 3, an annular ridge 95 movable into the annular groove 68 of the first component 6 is formed on the rear end face of the elastic cover 9. The annular ridge 95 has an inner peripheral face 95a and an outer peripheral face 95b which are inclined at equal angles so as to give the ridge 95 a width decreasing rearward. The inclination of the outer peripheral face 95b is smaller than that of the outer side face 68b defining the annular groove 68.

Although similar to the trapezoidal cross sectional form of the annular groove 68, the annular ridge 95 is slightly smaller than the groove 68 in cross sectional area.

The elastomer composition for forming the elastic cover 9 has incorporated therein a lubricating component having solid lubricity, such as paraffin wax or one of polyethylenes having varying degrees of polymerization, or a superfine spherical rigid lubricating component of polyethylene, nylon, Teflon or the like.

When required, the elastic cover 9 may have a projection 96 formed on the front end of the conical portion 91 and similar to that of the conventional cover as indicated in the dashed line in FIG. 1. When the syringe 2 is used, the projection 96 advances into a nozzle 30 at the front end of the syringe body, forcing out the entire quantity of the liquid agent within the syringe, thereby preventing waste.

With the elastic cover 9 fitted over the plunger body 5, a small clearance 90 is formed between the conical portion 81 of the plunger body 5 and the cover 9 as seen in FIG. 2. In the case of the cover 9 shown in FIG. 3, the rear end face of the annular ridge 95 is positioned substantially flush with the plane of opening of the annular groove 68 in the backplate 62.

The syringe body 3 is prefilled with the liquid agent to be injected and sealed by the plunger (4) at a rear portion thereof, and has its front nozzle 30 temporarily sealed so as not to permit leakage of the liquid agent. Before the syringe body 3 is filled with the liquid agent, the entire inner surface of the syringe body 3 is uniformly coated with a very small amount of liquid polydimethylsiloxane so as to render the plunger 4 smoothly slidable on the inner surface of the syringe 2. This liquid is usually known as a silicone oil, which is, for example, Silicone 360 Medical Fluid, product of Dow Corning Corporation.

The syringe body 3 is fixed in the socket 11 of the injector 1 in the same manner as in the prior art (see FIG. 10) by rotating the syringe body 3 with its rear end fitted in the socket 11, and positioning the ridge 31 of the syringe body 3 on the rear side of the syringe holding flange 12.

When the piston 13 is gradually projected, the hook 74 of each connecting piece 73 of the plunger 4 is engaged with the back side of the plunger holding piece 14 of the piston 13.

When the piston 13 is further projected, the plunger 4 advances, whereby the liquid agent filled in the syringe body 3 can be injected into the vascular system of the human body or animal from the nozzle 30 of the syringe body 3 through a tube (not shown).

Advantages of the Embodiment

When the plunger 4 is pushed forward under an extremely high pressure, the elastic cover 9 stretches rearward while sliding over the plunger body 5, and is forced in between the plunger body 5 and the inner surface of the syringe body 3 and compressed to a higher degree to produce an enhanced sealing effect. As this phenomenon spreads, the rear end of the cover 9 stretches rearward, ingressing into the annular groove 68 of the backplate 62 for escape.

The outer annular wall 68c defining the annular groove 68 has a wall thickness gradually decreasing toward the opening side of the groove 68, while the inside face 68b of the wall 68c is so inclined as to approach the axis of the plunger 4 as it extends toward the groove bottom. This enables the annular ridge 95 of the elastic cover 9 to smoothly ingress into the annular groove 68 to escape from confinement by being guided by the inclined inside face 68b of the annular wall 68c.

Accordingly, the structure of the invention eliminates the conventional problem that in the course of advance of the plunger 4, the rearwardly stretching portion of the elastic cover 9, which portion is prevented from escaping, wedges into a very small clearance between the outer periphery of the backplate 62 and the inner surface of the syringe body 3 to produce scraped-off fragments or other problems.

The elastic cover rear portion ingressing into the annular groove further fills up the annular groove 68 to press on the inner surface of the syringe body 3, producing a more improved sealing effect.

The liquid agent within the syringe body 3 can be injected into the vascular system of the human body or animal with a higher pressure than is available with the syringe 2 of International Publication No. WO 98/20920 described above, by virtue of the annular groove 68 of the plunger 4. Although a high pressure ranging from 87 kg/cm$^2$ to 98 kg/cm$^2$ is applied for injection, the elastic cover 9 of the plunger 4 releases no scraped-off fragments, or troubles such as failure of the plunger 4 to advance will not develop, thereby providing a plunger having high reliability.

It is preferable to use the arrangement of FIG. 12 for accommodating the syringe 2 in the reinforcing case or pressure jacket 200 for injecting the liquid agent. Alternately, however, a pressure jacket-less syringe (as shown in FIG. 10) can be used According to the embodiment, the plunger body 5 has the recessed portion 52 formed in its periphery between the truncated cone 82 and the backplate 62 and extending over the entire circumference thereof, and the inward flange 94 formed along the opening edge of the elastic cover 9 is fitted in the recessed portion 52. This holds the plunger body 5 and the elastic cover 9 assembled, obviating the likelihood that the elastic cover 9 will slip off the plunger body 5 before the plunger 4 is fitted into the syringe body 3.

With the embodiment, the elastic cover 9 is fitted over the plunger body 5 with a small clearance 90 formed between the cover 9 and the front end of the conical portion 81. This renders the cover 9 rearwardly stretchable with greater ease when the plunger 4 advances, permitting the cover 9 to be compressed to a higher degree at the head portion and inside the syringe body 3.

With the common syringe 2, liquid polydimethylsiloxane may be applied to the inner surface of the syringe body 3, wherein the liquid agent filled in the syringe body 3 could be forced out through the seal portion under the above-mentioned high pressure of 87 kg/cm$^2$ to 98 kg/cm$^2$ acting on the contact surface of the plunger 4. Further, it is likely that the polydimethylsiloxane is not transported to the portion of inner wall surface to be contacted with the syringe body 3 anew during the movement of the plunger 4, thus failing to maintain suitable lubricity.

According to the embodiment, the composition to be molded into the elastic cover 9 has incorporated therein a lubricating component, such as paraffin wax or polyethylene, having solid lubricity, or a superfine spherical lubricating component such as polyethylene, nylon or Teflon. Such a component often exhibits a phenomenon known as blooming, that is, the phenomenon of becoming distributed and separating out on the surface of the product during molding. This results in more effective lubricity than is otherwise attainable by the proportion of the lubricating component used, rendering the elastic cover 9 slidable more smoothly on the inner surface of the syringe body 3 and reducing the resistance to the injection by the plunger 4.

According to the embodiment, the plunger body 5 has the rearwardly flaring truncated cone 82 so as to compress the elastic cover 9 to a higher degree between the cone 82 and the inner surface of the syringe body 3 by a wedging effect with the advance of the plunger 4. However, the plunger body 5 is not limited to this construction; the outer peripheral portion of the plunger body 5 corresponding to the portion of the elastic cover 9 which is in contact with the inner surface of the syringe body 3 can be in the form of a cylindrical surface parallel to the inner surface of the syringe body 3. The plunger body 5 thus constructed is of course also effective for preventing the rear end of the elastic cover 9 from biting into the minute clearance between the outer periphery of the backplate 62 and the inner surface of the syringe body 3 and releasing scraped-off fragments.

In practicing the present invention, the front portion of the plunger body 5 is not limited to the conical portion 81 of the embodiment, but can be, for example, approximately hemispherical insofar as the front portion has a diameter gradually decreasing toward the front end.

Further in practicing the present invention, the side faces 68a, 68b defining the annular groove 68 in the front surface of the backplate 62 of the plunger body 5 need not always be inclined but can be so curved as to give the groove 68 a width decreasing toward the groove bottom. The backplate 62 can be increased in strength also in this case without giving an increased thickness to the groove-defining walls thereof.

The present invention is applicable similarly to syringes 2 of the type to be provided in an empty state filled with no liquid agent. When to be used, the syringe is filled with a liquid agent by moving the plunger 4 rearwardly of the syringe body 3 to draw the agent into the syringe body 3.

The syringe 2 of the present invention can be used also as connected to a mechanism which retracts the syringe body 3, with the plunger 4 held in a fixed position, to advance the plunger 4 relative to the syringe body 3.

What is claimed is:

1. A syringe comprising:

a cylindrical syringe body (3); and a plunger (4) movably disposed within the syringe body (3) for injecting a liquid agent filled in the syringe body (3) from the syringe body (3) into the vascular system of a human body or animal, the plunger (4) comprising a plunger body (5) and an elastic cover (9) fitted over the plunger body from the front, the plunger body (5) comprising a backplate (62) at a rear end thereof, the backplate (62) defining an annular groove (68) forwardly opened and formed in a front surface thereof in the vicinity of an outer periphery thereof, the elastic cover (9) comprising a portion to be rearwardly stretched by friction with the syringe body (3) during advancement of the plunger (4) and operable to ingress into the annular groove (68).

2. A syringe according to claim 1 wherein the elastic cover (9) further comprises an annular ridge (95) formed on a rear end face thereof and concentric with the elastic cover.

3. A syringe according to claim 1 wherein the backplate (62) further comprises opposite side faces (68a), (68b) defining the annular groove (68) and inclined to give the groove a width decreasing toward a bottom thereof.

4. A syringe according to claim 1 wherein the elastic cover (9) is molded from a composition having incorporated therein paraffin wax, or polyethylene.

5. A syringe according to claim 1 wherein the syringe body (3) is prefilled with the liquid agent to be injected, sealed by the plunger (4) at a rear portion thereof and provided at a front portion thereof with a nozzle (30) temporarily sealed so as not to permit leakage of the liquid agent.

* * * * *